US005304379A

United States Patent [19]

Cormier et al.

[11] Patent Number: 5,304,379
[45] Date of Patent: Apr. 19, 1994

[54] METHOD FOR REDUCING SENSITIZATION OR IRRITATION IN TRANSDERMAL DRUG DELIVERY AND MEANS THEREFOR

[75] Inventors: Michel J. N. Cormier, Palo Alto; Philip W. Ledger, Mountain View; Alfred Amkraut, Palo Alto, all of Calif.; Jean P. Marty, Sceaux, France

[73] Assignee: Alza Corporation, Palo Alto, Calif.

[21] Appl. No.: 945,205

[22] Filed: Nov. 3, 1992

Related U.S. Application Data

[60] Division of Ser. No. 642,691, Jan. 7, 1991, abandoned, which is a continuation of Ser. No. 391,805, Aug. 8, 1989, abandoned, which is a division of Ser. No. 162,777, Mar. 1, 1988, Pat. No. 4,885,154.

[51] Int. Cl.$^5$ ............................................. A61F 13/00
[52] U.S. Cl. .................................. 424/449; 424/448; 514/946
[58] Field of Search ................... 424/448, 449; 514/946

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 4,006,218 | 2/1977 | Sipos | 424/54 |
| 4,087,538 | 5/1978 | Portnoff | 424/274 |
| 4,144,317 | 3/1979 | Higuichi et al. | 424/21 |
| 4,286,592 | 9/1981 | Chandrasekan | 128/260 |
| 4,314,557 | 2/1982 | Chandrasekan | 128/260 |
| 4,379,454 | 4/1983 | Campbell et al. | 604/897 |
| 4,440,778 | 4/1984 | Matsui et al. | 424/274 |
| 4,559,222 | 12/1985 | Enscore et al. | 424/28 |
| 4,573,995 | 3/1986 | Cheng et al. | 604/896 |
| 4,573,996 | 3/1986 | Kwiatek et al. | 604/897 |
| 4,645,774 | 2/1987 | Toth et al. | 514/317 |

FOREIGN PATENT DOCUMENTS

| | | | |
|---|---|---|---|
| 0117080A2 | 8/1984 | European Pat. Off. | A61K 7/48 |
| 0156565A2 | 10/1985 | European Pat. Off. | A61L 15/03 |
| 0190449A1 | 8/1986 | European Pat. Off. | C09D 7/12 |
| 1001949 | 8/1965 | United Kingdom | A61K 3/00 |

OTHER PUBLICATIONS

Lui et al, "Quantitative Mechanistic Studies on Inhibition of Transdermal Metabolism of B-estradiol by Ethanol," Journal of Pharmaceutical Sciences vol. 76, No. 11, Nov. 1987 (abstract).

Drill's Pharmacology in Medicine, ed. Joseph R. DiPalma, Third edition, pp. 41–42 (1965).
Medicinal Chemistry, ed. Alfred Burger, Third edition, pp. 56–57 (1970).
I. S. Severina, "Effect of Alcohols on Mitochondrial Monoamine Oxidase Activity," Bull. Exp. Biol. & Med., 79 (1), pp. 30–32 (1975).
A. Pannatier et al, "The Skin as a Drug-Metabolizing Organ," Drug Metabolism Reviews, 8(2), pp. 319–343 (1978).
E. A. Zeller et al., "How Do MAO-A and MAO-B Select their Substrates? Thermodynamic Aspects," Function and Regulation of Monoamine Enzymes: Basic and Clinical Aspects, E. Usdin et al editors, pp. 469–476 (1981).
C. J. Fowler et al, "Selective Inhibitors of Monoamine Oxidase A and B: Biochemical, Pharmacological, and Clinical Properties," Medicinal Research Reviews, vol. 4, No. 3, pp. 323–358. (1984).
P. K. Noonan, "Cutaneous Metabolism of Xenobiotics," Percutaneous Absorption, R. L. Bronaugh et al., editors, pp. 65–85 (1985).
Goodman and Gilman's, "The Pharmacological Basis of Therapeutics," Seventh edition pp. 13–21 (1985).
Goodman and Gilman's, "The Pharmacological Basis of Therapeutics," Seventh edition, pp. 423–426 (1985).
R. J. Martin et al, "Skin Metabolism of Topically Applied Compounds," International Journal of Pharmaceutics, vol. 39, pp. 23–32 (1987).
D. L. J. Opdyke, Inhibition of Sensitization Reactions induced by Certain Aldehyde FD. Cosmet. Toxicol. vol. 14, pp. 197–198 (1976).
J. D. Guin et al., "The Effect of Quenching Agents on Contact Urticaria Caused by Cinnamic Aldehyde," J. Amer. Aca. Derm., vol. 10, No. 1, pp. 45–51 (1984).

Primary Examiner—Thurman K. Page
Assistant Examiner—Jyothsna Venkat
Attorney, Agent, or Firm—Jean M. Duvall; D. Byron Miller; Steven F. Stone

[57] ABSTRACT

A method and means for reducing sensitization or irritation caused by transdermally delivered drugs, wherein one or more metabolic modulators is coadministered with a sensitizing or irritating drug.

10 Claims, 2 Drawing Sheets

METHOD FOR REDUCING SENSITIZATION OR IRRITATION IN TRANSDERMAL DRUG DELIVERY AND MEANS THEREFOR

CROSS-REFERENCE TO RELATED APPLICATION

This application is a division of U.S. Ser. No. 07/642,691 filed Jan. 7, 1991, now abandoned which application is a continuation of 07/391,805 filed Aug. 8, 1989, now abandoned, which application is a division of 07/162,777, filed Mar. 1, 1988 now issued as U.S. Pat. No. 4,885,154, which applications are incorporated herein by reference, and benefit is claimed by their filing dates. This invention is related to the invention disclosed in the copending, coassigned patent application of Robert Gale et al, for Anesthesia and Antisepsis of the Skin, identified as U.S. Ser. No. 07/162,761 of filing date Mar. 1, 1988, now abandoned which is a continuation-in-part of U.S. patent application Ser. No. 06/829,368 filed on Feb. 13, 1986 now abandoned. These applications are assigned to the ALZA Corporation of Palo Alto, Calif.

FIELD OF THE INVENTION

This invention relates to the transdermal delivery of drugs. More particularly, this invention relates to the modification, reduction or elimination of sensitization or irritation cause by the metabolism or biotransformation of a sensitizing of irritating drug being delivered transdermally. Still more particularly, but without limitation thereto, this invention relates to the coadministration of a drug with one or more metabolic modulators capable of modifying the drug's metabolism in the skin, thereby reducing sensitization or irritation.

DESCRIPTION OF TERMS

As used herein, the term "drug" relates to a biologically active agent, compound or composition of matter which is administered for the purpose of providing some beneficial or therapeutic effect. As used herein, the term "transdermal" delivery relates to the delivery of agents of passage through skin or mucosa by topical application. As used herein, the term "metabolic modulator" relates to an agent which is capable of modifying the metabolism of a drug or therapeutic agent in the skin or mucosa, so as to inhibit the formation of reactive or irritating metabolites.

BACKGROUND OF THE INVENTION

When therapeutic drugs are administered, body metabolism performs a series of reactions which change the chemical structure of the administered drug. Typically, the drug will be metabolized by more than one pathway. In this manner, the drug is bioconverted, either partially or completely, into its intermediates or metabolites. This is known as biotransformation. The chemical reactions occurring during biotransformation of a drug are classified as phase-I and phase-II. Phase-I reactions are functionalization reactions and involve the conversion of the drug to its metabolites by oxidation, reduction or hydrolysis. Phase-II reactions are conjugation reactions and involve the coupling between the drug or its metabolite and an endogenous substrate.

Although initially described in the liver (see Goodman and Gilman's The Pharmacological Basis of Therapeutics, pp. 13-21, 7th edition, 1985) and in other internal organs, it is now known that biotransformation enzymes are also present in the cells of the skin. During transdermal delivery of a drug, a portion of drug may become altered by the action of these enzymes. In fact, the very presence of the drug may cause levels of enzymes to increase due to the phenomenon of induction. This contributes to the drug's biotransformation.

The biological function of biotransformation is to facilitate elimination of the drug, since generally the metabolites formed are more water soluble than the drug and thus are more readily excreted. However, it is known that some intermediates in the chemical pathway can be more reactive than the parent compound, and thus may tend to react with tissue constituents and be retained for longer periods of time.

It is known in the art that the activity of drug-metabolizing enzymes can be modified by administration of metabolic modulators. For example, the activity of monoamine oxidases in the brain is associated with depression and the activity of these enzymes can be affected by the administration of anti-depressant metabolic modulators. This type of therapeutic administration of metabolic modulators to humans has been mainly for the purpose of affecting the metabolism of endogenous compounds, i.e. those which occur naturally in the body. The inventors are, however, unaware of any disclosure teaching the administration of metabolic modulators for the specific purpose of reducing sensitization or irritation by inhibiting the metabolism of externally applied drugs in the skin or mucosa.

SUMMARY OF THE INVENTION

The inventors believe that the sensitization (allergic contact dermatitis) or irritation that accompanies the transdermal administration of some drugs is caused by the biotransformation of the drug in the skin. An irritant reaction occurs if irritating metabolites are formed, which can react adversely with cellular components. Alternately, sensitization or contact dermatitis occurs if reactive metabolites are formed, which can provide a configuration capable of activating the immune system.

In transdermal drug therapy it is desirable to reduce or avoid sensitization or irritation. The inventors believe that by modifying the metabolism that causes the formation of undesirable metabolites, this result can be achieved.

An object of this invention is to transdermally deliver a drug whereby the full beneficial value of said drug is realized and at the same time any sensitization or irritation associated with said drug is eliminated by coadministering one or more metabolic modulators which inhibits formation of any undesirable metabolites.

An object of this invention is to provide a method for the reduction or elimination of sensitization and irritation responses to drugs and other agents being administered transdermally wherever such drugs form reactive or irritating metabolites by means of skin metabolism.

A further object of this invention is to simultaneously administer a drug and one or more metabolic modulators capable of modifying the drug's metabolism.

A still further object of this invention is to incorporate a drug and one or more metabolic modulators therefor, into a transdermal drug delivery system.

These and other objects, features and advantages have been demonstrated by the present invention wherein a medical device for the administration of a drug susceptible to being metabolized in the skin or mucosa, for the prevention of undesirable side effects in the skin or mucosa, generated by said drug being transdermally administered, is comprised of, in combination: a reservoir means containing the drug, a reservoir means containing one or more metabolic ,modulators capable of modifying the skin or mucosal metabolism of the drug (which may be combined with the drug reservoir in some embodiments) and means for maintaining said reservoir means in drug and metabolic modulator transmitting relationship to the skin or mucosa. This invention also encompasses a composition of matter and a method of treatment.

DESCRIPTION OF THE INVENTION

Figure 1:
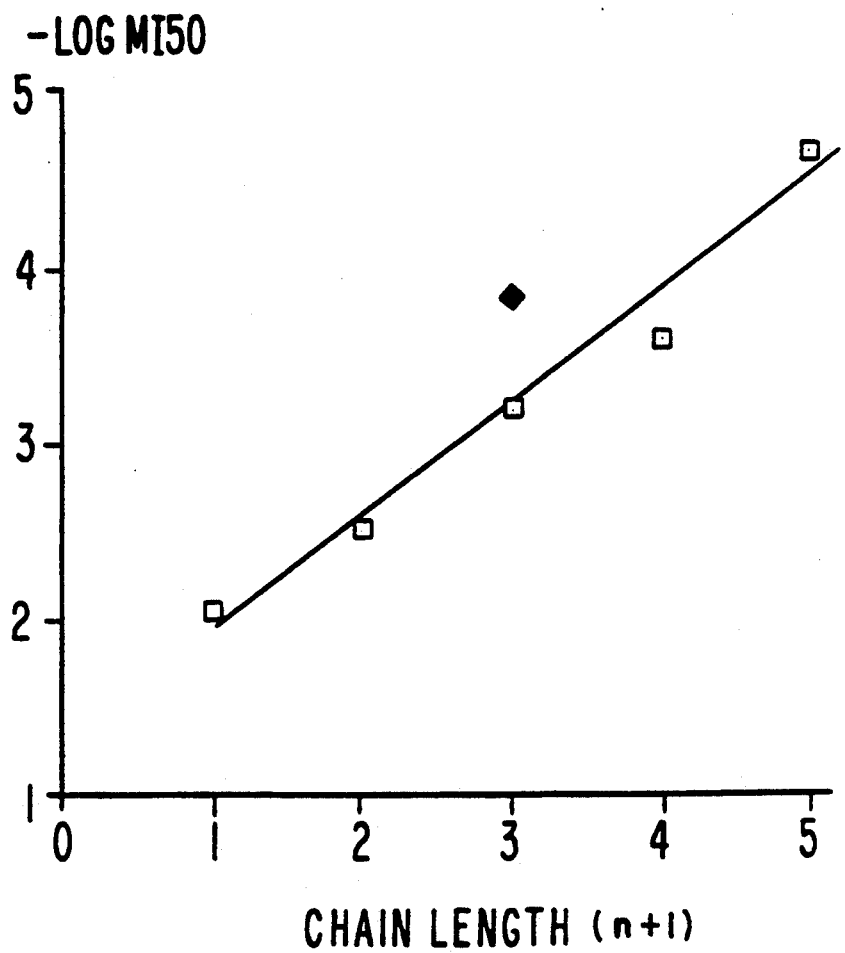
FIG. 1 is a graph illustrating propranolol metabolism inhibition by aromatic alcohols in relation to chain length.

This invention is applicable to prevent the formation of reactive or irritating metabolites regardless of the pathway by which they can be formed, by modifying the enzymatic activity involved. Some enzymes are responsible for the formation of reactive metabolites which can lead to sensitization. Other enzymes are responsible for the formation of irritating metabolites which can lead to irritation. Both types of enzymatic activity can be modified and thus avoid the undesirable side effects of irritation and sensitization.

Enzymes known to be present in the skin or mucosa include, without limitation, monoamine oxidases, mixed function oxidases of the cytochrome $P_{450}$ series of isozymes, peroxidases, decarboxylases (for example, DOPA decarboxylase), carboxyl esterases, adenosine deaminases, epoxide hydrolases, aldehyde dehydrogenases and alcohol dehydrogenases.

These enzymes also are active in the body itself, such as in the liver and brain and their activity is known to be inhibited in the body by a variety of compounds. For example, mixed function oxidase activity can be inhibited by imidazole derivatives such as cimetidine, alcohol dehydrogenase activity can be inhibited by 4-methyl pyrazole and aldehyde dehydrogenase activity can be inhibited by cyanamide.

Not all enzymatic activity results in the formation of irritating or reactive metabolites. However, when such activity has this result, the activity can be modified according to this invention to prevent the formation of any undesirable metabolites.

This invention involves the coadministration, preferably from a transdermal therapeutic system, of a drug and one or more metabolic, modulators that will interfere with the action of biotransformation enzymes that could potentially metabolize the drug. The result of such coadministration is to reduce the irritant or sensitizing potential of the drug's metabolites.

The transdermal route of parenteral delivery of drugs provides many advantages and transdermal systems for delivering a wide variety of drugs or other beneficial agents are well known in the art. Typical systems are described in U.S. Pat. Nos. 3,598,122, 3,598,123, 4,286,592, 4,314,557, 4,379,454, 4,559,222 and 4,573,995, for example, all of which are incorporated herein by reference. The coadministration of a metabolic modulator and a drug as disclosed herein can be accomplished using transdermal systems of this type.

According to our invention, one or more metabolic modulators and the sensitizing or irritating drug to be delivered, are placed in drug and metabolic modulator transmitting relationship to the appropriate body surface, preferably suspended in a carrier therefor, and maintained in place for the desired period of time. The drug and metabolic modulator are typically dispersed within a physiologically compatible matrix or carrier which may be applied directly to the body as an ointment, gel, cream, suppository or sublingual or buccal tablet, for example, but are more preferably administered from a transdermal therapeutic system.

The drug is delivered at a therapeutic rate and the modulator(s) at a metabolism modifying rate(s), for a predetermined time. The relevant time frame varies with the regimen of drug administration involved. Some drugs need to be administered continuously for days and in that instance a suitable transdermal system would have sufficient drug and modulator to provide the necessary rates of delivery of up to 24 hours for systems which are replaced periodically, or up to a week, for longer duration systems. Some drugs only need to be administered once and in that instance, a suitable transdermal system would have sufficient drug and modulator to provide the necessary rates of delivery for a few hours.

This invention involves the coadministration of a drug that is susceptible to being metabolized in the skin or mucosa and one or more metabolic modulators that will modify or inhibit that metabolism. It is important to note that this invention is not limited to any particular transdermal system, as are commonly known in the art. Nor is this invention limited to a particular formulation. Therefore, the embodiments described herein and in the accompanying figures, are merely illustrative and are not intended to limit the scope of the invention in any manner.

There are numerous drugs which are known to sensitize or irritate the skin, when administered transdermally. The metabolic modifier selected will depend on the enzyme responsible for the drug's metabolism. As stated above, it is known that there are numerous enzymes responsible for drug metabolism in the skin. For example, it is known that drugs having primary or secondary amine moieties are subject to deamination by the activity of monoamine oxidases. Tertiary amines are indirectly subject to monoamine oxidase activity because they must first undergo N-dealkylation by dealkylases before they can undergo deamination by monoamine oxidases.

Many compounds which are effective as therapeutic agents or drugs are amines and this invention will be described with respect to drugs containing this moiety. It should be recognized however, that the invention is broadly applicable to any moiety which is metabolized after administration to provide irritation or sensitization. According to this invention, the deamination of transdermally administered amine drugs can be prevented by modifying the activity of monoamine oxidases.

Typical monoamine oxidase inhibitors which act on internal tissues such as the liver and brain are listed at great length in C. J. Fowler and S. B. Ross, "Selective Inhibitors of Monoamine oxidase A and 8: Biochemical, Pharmacological, and Clinical Properties" in MEDICAL RESEARCH REVIEWS, Vol. 4, No. 3, pp. 323-358 (1984). According to this invention these compounds are administered transdermally to modify monoamine oxidase activity in cutaneous metabolism. These compounds include, without limitation, α-ethyl substituted monoamines such as amiflamine, harmala alkaloids such as harmine, tetrahydro-β-carbolines such as 6-hydroxytetrahydro-β-carboline, oxazolidinone derivatives such as cimoatone, benzylamine and aliphatic amine analogues, benzyl alcohol, aliphatic alcohols and amitriptyline, acetylenic compounds such as clorgyline and 1-deprenyl, cyclopropylamines such as tranylcypromine, and hydrazines such as phenylhydrazine.

According to this invention monoamine oxidase inhibitors can be used to modify monoamine oxidase activity in conjunction with the transdermal administration of amine drugs which are subject to metabolism by monoamine oxidases. These include, without limitation, transdermally administratable β-adreno receptor blocking drugs such as propranolol metoprolol, timolol, oxprenolol and pindolol, along with antihistamines such as chlorpheniramine and local anesthetics such as tetracaine.

The β-adreno receptor blocking drug, propranolol, has been found to sensitize human subjects after several cutaneous applications, thereby limiting its usefulness as a transdermally administered drug. We have studied the metabolism of this drug by keratinocytes, in vitro (human skin and isolated skin cells in culture) and believe that discussion of its metabolism will aid understanding of this invention. Propranolol has the following structure:

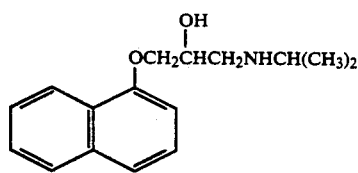

Our studies have shown that in the skin, the metabolism pathway of propranolol is as follows:

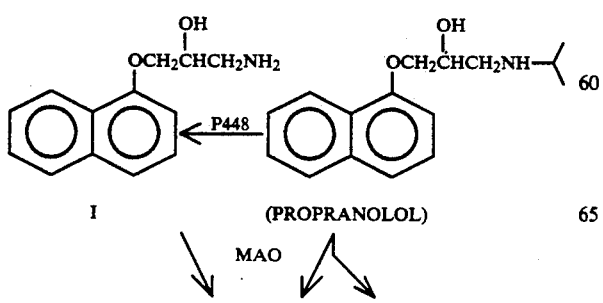

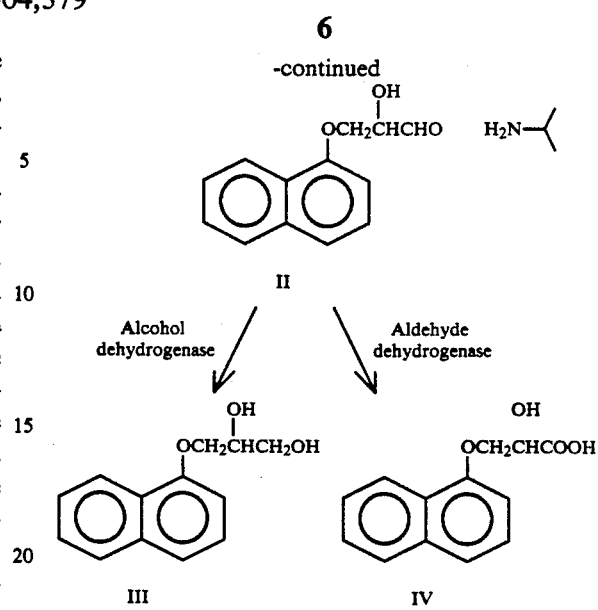

Metabolites I, III and IV have been detected and our studies with metabolic inhibitors have shown the importance of monoamine oxidases and cytochrome $P_{448}$ (an isozyme of the $P_{450}$ group) in the skin metabolism of propranolol.

The inventors believe that the observed sensitization to propranolol was caused by reactive metabolites formed during its biotransformation, such as the unstable, short lived and potentially reactive metabolite II and that the key enzymes in the generation of this metabolite were the monoamine oxidases. Tranylcypromine, commonly administered as an anti-depressant, produces its anti-depressant effect by inhibition of monoamine oxidase activity in the brain. The inventors have found that tranylcypromine inhibits propranolol metabolism, thus establishing that monoamine oxidases were indeed involved. This is shown by the following example.

EXAMPLE I

Human keratinocytes were incubated in tritiated propranolol (12.5 Ci/mmole, final concentration $1.5 \times 10^{-7}M$) and tranylcypromine. At the end of several days, the metabolites resulting from propranolol metabolism were identified and quantitated by thin layer chromatography. This was compared to metabolism in a control incubation, which did not have any tranylcypromine added. Thus it was determined in this comparison that tranylcypromine inhibited the propranolol, metabolism.

The metabolism of propranolol is also inhibited with simple, less potent molecules which are preferred for incorporation into a composition for topical application or into a transdermal delivery device. These compounds include phenyl alcohols having the general formula:

$$(C_6H_5)\text{—ROH}$$

where R is selected from the group consisting of:

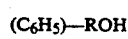

where n=0-4, and

$CH=CHCH_2$.

It has been found that there is a linear correlation between inhibitory activity and the length of the hydrocarbon chain from phenyl methanol (n=O) to 5-phenyl-1-pentanol (n=4). This is illustrated in the following example and FIG. 1, where inhibitory activity was measured by the dose (molarity) of agent required to inhibit 50% of drug metabolism.

EXAMPLE II

Human keratinocytes were incubated in tritiated propranolol (12.5 Ci/mmole, final concentration $1.5 \times 10^{-7}M$) and a range of concentration of each phenyl alcohol. Quadruplicates were used at each concentration. At six days, the metabolites resulting from propranolol deamination were extracted (ether, pH of 3) and the radioactivity of the extract was measured by scintillation counting. The concentration of each phenyl alcohol studied, which inhibits 50 percent of propranolol metabolism (MI50) was estimated by means of the Litchfield and Wilcoxon method. Results are expressed in FIG. 1 as a function of the number of carbon atoms between the phenyl ring and the hydroxy group. The chain length is then expressed as "n+1".

One embodiment of this invention is the transdermal delivery of a sensitizing or irritating drug and a metabolic modulator by application of a formulation to the skin surface, which may be aqueous or non-aqueous based. These formulations can be designed to deliver the drug and the metabolic modulator at the desired fluxes and can be in numerous forms in which the drug and metabolic modulator are suspended in a carrier. These include without limitation, ointments, gels and creams, along with transdermal therapeutic systems.

Aqueous formulations, specifically gels, typically comprise water and about 1-2 weight % of a gelling agent such as hydroxyethyl cellulose or hydroxypropyl cellulose. Typical non-aqueous gels are comprised of silicone fluid or mineral oil, the latter of which may also have 1-2 weight % of a gelling agent such as colloidal silicon dioxide. The suitability of a particular gel depends upon the compatibility of its constituents with both the drug and the metabolic modulator, along with the permeation enhancer, if any. Typical gel formulations are shown in Examples III and IV.

EXAMPLE III

A human subject suspected of being sensitized to propranolol was patch tested for 16 hours with 0.5% propranolol in a 2% hydroxyethyl cellulose (HEC) gel buffered to a pH of 8.5 with 0.05M TrisHC1. One to two days later the subject developed a reaction which was characteristic of a contact sensitization reaction (elicitation). This confirmed that the subject was sensitized to propranolol. Therefore, subsequent exposure to propranolol would again result in an elicitation reaction.

The same subject was patch tested several days later with the following compositions in 2% HEC gel buffered to a pH of 8.5 with 0.05M TrisHC1: 0.5% propranolol; 0.5% tranylcypromine; 10% 2-phenyl-1-ethanol; 0.5% propranolol with 0.5% tranylcypromine; and 0.5% propranolol with 10% 2-phenyl-1-ethanol. Each composition was placed simultaneously at different sites on the subject's volar forearm. One day later, a strong reaction was observed only at the propranolol site. No reaction occurred at the other sites, nor did they appear at any time during the resolution of the positive reaction.

As shown in Example III, 10 weight percent is a suitable amount of metabolic modulator for use in a gel formulation. For purposes of this invention, a suitable range is 0.1-20 wt %, preferably 2-10 wt %. These ranges are appropriate for both topical formulations as shown in Example III and the transdermal systems described below.

The drug is preferably present in an amount sufficient to provide administration at a therapeutically effective rate for a predetermined time and the modulator(s) is preferably present in an amount sufficient to provide administration at a metabolic modifying rate for a predetermined time. To achieve this, typically the drug and metabolic modulator are dispersed through the carriers in excess of saturation, the amount of excess being a function of the intended useful life of the system. They may, however, be present at initial levels below saturation without departing from this invention. In some instances, it may be necessary to have the modulator delivered simultaneously with the drug so that as long as drug is present in the skin and thus subject to being metabolized, the metabolic modulator is also present. This may not always be the case, and this invention contemplates other patterns of delivery.

Methods used in the propranolol studies were also applied to tetracaine, which has the structure:

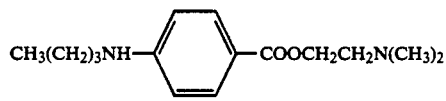

Evidence was obtained for the existence of several metabolic pathways for this drug, of which an appreciable portion (25%) was monoamine oxidase-dependent and could be inhibited, in vitro, by tranylcypromine and 2-phenyl-1-ethanol. The ability of enzyme inhibitors to inhibit elicitation of reactions to this drug were then tested.

EXAMPLE IV

Two human subjects who were known to be sensitized to tetracaine were patch tested with the following compositions on a weight percent basis, in 2% HEC gel buffered to a pH of 8.0: 2% tetracaine (positive control); 2% tetracaine plus 1.25%, 2.5%, 5% and 10% 2-phenyl-1-ethanol; 2% tetracaine plus 1.25%, 2.5%, 5% and 10% 3-phenyl-1-propanol; 2% tetracaine plus 5% 4-phenyl-1-butanol; 2% tetracaine plus 1.25%, 2.5% and 5% cinnamyl alcohol.

Testing occurred over a period of several weeks where a positive control composition was placed on the skin along with one of the tetracaine/phenyl alcohol compositions and the intensity of the skin reaction obtained, was observed. This was repeated on different areas of the arm until all of the compositions were tested. Each formulation remained on the skin for a period of three hours and the reactions were observed during the 16-24 hour period after removal of the formulation. Erythema or redness of the reaction site was quantitated with a Minolta Chromameter. In all instances, the intensity of the reaction caused by the tetracaine/phenyl alcohol composition, was less than that caused by tetracaine alone (positive control). Thus it was established that the presence of phenyl alcohols reduced the elicitation reaction as compared to the 2% tetracaine gel.

The best results were obtained using 2-phenyl-1-ethanol and 3-phenyl-1-propanol. On a scale of 0–100, with 0 being 0% inhibition (2% tetracaine gel/positive control) and 100 being 100% inhibition (placebo gel/negative control), the following data was obtained 21 hours after removal of the formulations:

| Weight % Inhibitor | Percent Inhibition of Reaction | |
|---|---|---|
| | 2-Phenyl-1-ethanol | 3-Phenyl-1-propanol |
| 2.5 | 52 | 37 |
| 5 | 52 | 100 |
| 10 | 77 | 100 |

EXAMPLE V

Methods used in the propranolol studies were applied to chlorpheniramine which has the following structure:

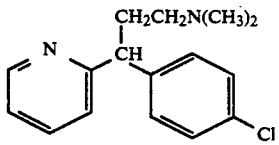

It was again found that the in vitro metabolism of chlorpheniramine in the skin is also largely dependent upon monoamine oxidase activity. Therefore, the metabolism of chlorpheniramine can also be inhibited in the skin or mucosa, by the addition of metabolic modulators such as the phenyl alcohols disclosed with reference to propranolol.

Figure 2:
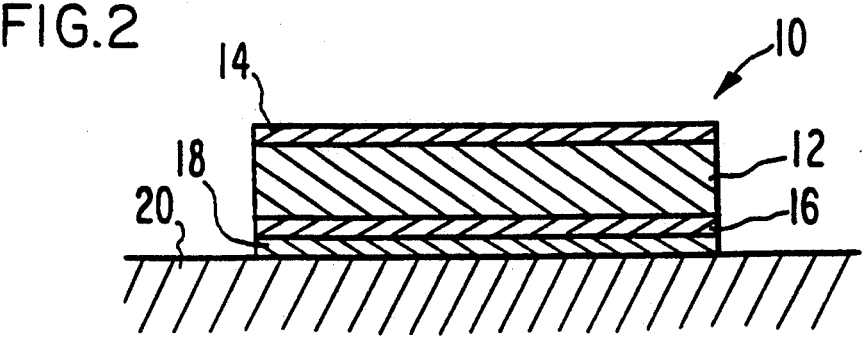
FIG. 2 is a cross-sectional view of one embodiment of a transdermal therapeutic system according to this invention having a rate controlling membrane and an in-line contact adhesive.

Referring now to FIG. 2, a transdermal therapeutic system 10 according to this invention is shown. The system 10 comprises a drug reservoir 12 covered by an impermeable backing 14, and an optional drug rate controlling membrane 16. Membrane 16 is comprised of a microporous or other rate controlling material. A typical example is microporous polypropylene. The system 10 adheres to the surface of the skin 20 by means of an in-line contact adhesive 18. The adhesive layer 13 is comprised of a pharmaceutically acceptable adhesive as is known in the art and contains a set amount of one or more metabolic modulators. A strippable release liner, not shown, adapted to be removed prior to application would normally be included in the packaged product.

Figure 3:
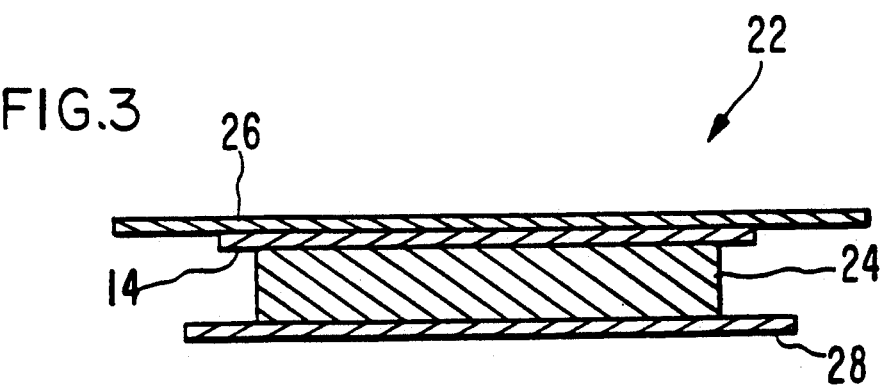
FIG. 3 is a cross-sectional view of another embodiment of this invention having an adhesive overlay.

In an alternate embodiment, the system is attached by means of an adhesive overlay, as is shown in FIG. 3. The system 22 is comprised of a drug/metabolic modulator(s) reservoir 24 which is in the form of a matrix or carrier having the drug and the metabolic modulator dispersed throughout. The reservoir 24 is covered by an impermeable backing 14 which is preferably sized larger in circumference than the reservoir 24. Means 26 for maintaining the system on the skin may be fabricated together with or provided separately from the remaining elements of the system. Means 26 as illustrated in FIG. 3, takes the form of a pharmaceutically acceptable adhesive overlay. A strippable release liner 28 would also be provided with the system 22, to be removed prior to use.

Various materials suited for the fabrication of the various layers are disclosed in the aforementioned patents. The composition of the matrix may, depending on the drug to be delivered, be either an aqueous or anhydrous base. Suitable matrices or carriers are described in the above identified patents and include, without limitation, natural and synthetic rubbers such as polybutylene, polyisobutylene, polybutadiene, polyethylene, styrene-butadiene copolymers, polyisoprene, polyurethane, ethylene/propylene copolymers, polyalkylacrylate polymers, copolyesters, ethylene/acrylic copolymers, silicones and butadiene/acrylonitrile copolymers for example and other polymers such as the ethylene vinyl acetate (EVA) polymers described in U.S. Pat. No. 4,144,317 (which is incorporated herein by reference). Other suitable materials include gelled or thickened mineral oil, petroleum jelly and various aqueous gels and hydrophilic polymers. Typically, the drug is dispersed through the matrix or carrier at a concentration in excess of saturation, the amount of excess being a function of the intended useful life of the system. The drug may, however, be present at initial levels below saturation without departing from this invention.

The backing materials suitable for use in this invention include without limitation, polypropylene, polyester, polycarbonate, polyurethane or other polymer films.

In addition to the drug and the metabolic modulator(s), which are essential to the invention, the matrix may also contain other materials such as dyes, pigments, inert fillers, excipients and other conventional components of pharmaceutical products or transdermal therapeutic systems known to the art. A permeation enhancer may also be used to increase the penetration of the drug or the modulator into the skin or mucosa.

Figure 4:
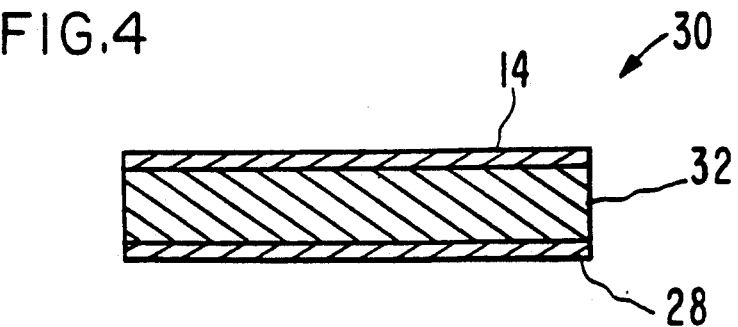
FIG. 4 is a cross-sectional view of still another embodiment of this invention having a self adhering matrix.

Another embodiment is shown in FIG. 4. System 30 is comprised of a self adhering matrix 32 and backing member 14. Matrix 32 contains both the drug and metaboltic modulator(s). Suitable matrix materials include poly(styrene-butadiene) and poly(styrene-isoprene-styrene) block copolymers, and high and low molecular weight polyisobutylene copolymers. The matrix may also be of an ethylene vinyl acetate (EVA) copolymer of the type described above.

Adhesive properties are enhanced by adding a resinous tackifier. This is especially important when using a non-tacky polymeric matrix. Examples of suitable tackifiers include: STAYBELITE ESTER #5 or #10, REGAL-REZ and PICCOTAC (all of which are trademarks of Hercules of New Jersey). Additionally, the matrix may also contain a rheological agent, suitable examples of which include, without limitation, mineral oil and silica.

The embodiment of FIG. 4 also contemplates the addition of a drug rate controlling membrane.

Inclusion of the metabolic modulator(s) can be in the drug reservoir and/or other drug releasing compartment of a transdermal therapeutic system so as to deliver the metabolic modulator at a different time or at a different rate than the drug. In some instances, there is great disparity between the drug flux and the metabolic modulator flux. In such cases, the metabolic modulator is preferably placed in the adhesive, as in FIG. 3. On the other hand, when there is no great disparity in fluxes, both the drug and the metabolic modulator may be placed together in the reservoir, as in FIG. 2.

Generally, elicitation occurs from doses lower than those required to induce sensitization. Therefore, it is likely to be more difficult to inhibit elicitation as was shown in Examples III and IV than to inhibit the actual induction of sensitization and this was studied in the following example.

EXAMPLE VI

In order to demonstrate that this invention can prevent the induction phase of contact sensitization, tetracaine/2-phenyl-1-ethanol patches were made according to this invention. These patches had the following composition by weight percent: 20.4% polystyrene-iso-prene-styrene) block copolymer (KRATON 112 Rubber, Shell Oil Company), 50.9% tackifier (REGAL-REZ 1094, Hercules), 13.0%, mineral oil, 0.7% antioxidant (IRGONOX 1010, Ciba-Geigy Corporation), 7.0% 2-phenyl-1-ethanol and 8.0% tetracaine base. The components were blended in an internal mixing bowl at 100° C. and after approximately one hour, the mixture was extruded between two release substrates. One substrate was peeled away and a backing member was applied in its place. Testing of these systems at 32° C. indicated that the in vitro flux in mg/hr/cm across cadaver epidermis was as follows:

| Time | 2-Phenyl-1-ethanol flux | Tetracaine flux |
|---|---|---|
| 0–1 hr | 133 | 52 |
| 1–2 hrs | 74 | 37 |
| 2–3 hrs | 52 | 29 |

Similar patches were manufactured without the presence of 2-phenyl-1-ethanol. These systems were comprised of the following, on a weight percent basis: 21.7% polyisobutylene (mw 1200k); 47.9% polyisobutylene (mw 35K); 25% light mineral oil; and 6% tetracaine. Testing of these systems at 32° C. indicated that the in vitro flux in $\mu g/hr/cm^2$, across cadaver epidermis was as follows:

| Time | Tetracaine flux |
|---|---|
| 0–1 hr | 56 |
| 1–2 hrs | 41 |
| 2–3 hrs | 31 |

Two groups of 100 human subjects each were then tested. They were each tested by application of a system, for a three hour duration, once every 8 weeks.

100 subjects were given the patches containing only tetracaine. Of these, 7 subjects (7%) exhibited a sensitization reaction. The other 100 subjects were given the patches containing both tetracaine and 2-phenyl-1-ethanol. Of these, 2 subjects (2%) exhibited a sensitization reaction. From these results, it was established that the presence of a metabolic modulator, in this instance 2-phenyl-1-ethanol, reduced the incidence of sensitization by about 70%.

Although this invention has been described with respect to monoamine oxidases as the enzymes to be inhibited, it is understood that this invention is applicable to the use of inhibitors of other metabolic enzymes that are implicated in the cutaneous metabolism of drugs in general and of substituted amines in particular. For example, isozymes of the cytochrome $P_{450}$ group can be responsible for N-dealkylation as in the formation of metabolite I from propranolol. In fact, often the drug itself is not a direct substrate for monoamine oxidases (for example, tertiary amines) and modification by other enzymes (for example, N-dealkylation) is required before monoamine oxidase-dependent deamination can occur. Thus, it is obvious that for some drugs, the inhibition of sensitization could be achieved by the use of enzyme inhibitors other than monoamine oxidase inhibitors.

This invention has been described in detail with particular reference to certain preferred embodiments thereof, but it will be understood that variations and modifications can be effected within the spirit and scope of the invention.

What is claimed is:

1. A device for the transdermal administration at a therapeutically effective rate, of a drug which is susceptible in metabolism by an enzyme present in the skin or mucosa and formation of a sensitizing or irritating drug metabolite when the drug is transdermally administered to a human in need thereof, which device comprises:
    (a) a reservoir comprising a drug tetracaine in an amount and in a form sufficient to provide transdermal administration in a therapeutically effective amount over a predetermined period of time at a selected skin or mucosa site and a metabolic modulator selected from the group consisting of tranylcypromine and phenyl alcohols having the structure $(C_6H_5)$—R—OH, where R is selected from the group consisting of: —$(CH_2)_n CH_2$— where n=0–4, and —CH—$CHCH_2$— capable of inhibiting the monoamine oxidase enzyme that metabolizes the drug, in an amount and in a form sufficient to inhibit the metabolism of the drug by the enzyme at the selected site during all of the predetermined period of time during which the drug is transdermally administered, and thereby inhibit the formation of the sensitizing or irritating drug metabolite;
    (b) a backing on the skin or mucosa-distal surface of the reservoir; and
    (c) means for maintaining the reservoir in drug and metabolic modulator transmitting relationship to the skin or mucosa.

2. The device of claim 1, wherein the drug is dispersed in the reservoir in excess of saturation.

3. The device of claim 1, wherein the metabolic modulator comprises about 0.1–20 wt. % of the device.

4. The device of claim 1, wherein the metabolic modulator comprises about 2–10 wt. % of the device.

5. The device of claim 1, wherein the metabolic modulator is selected from the group consisting of tranylcypromine, 2-phenyl-1-ethanol, 3-phenyl-1-propanol, 4-phenyl-1-butanol and cinnamyl alcohol.

6. The device of claim 1, further comprising an effective amount of a second metabolic modulator selected from the group consisting of tranylcypromine and phenyl alcohols having the structure $(C_6H_5)$—R—OH, where R is selected from the group consisting of: —$(CH_2)_n CH_2$— where n=0–4, and —CH=$CHCH_2$—.

7. The device of claim 1, wherein the means for maintaining the reservoir in relation with the skin or mucosa comprises an in-line adhesive layer on the skin-proximal surface of the reservoir.

8. The device of claim 1, wherein the means for maintaining the reservoir in relation with the skin or mucosa comprises an adhesive overlay.

9. The device of claim 1, wherein the means for maintaining the reservoir in relation with the skin or mucosa is a self-adhering means composition.

10. The device of claim 1, wherein the metabolic modulator is contained with the adhesive.

* * * * *